US010064988B2

(12) United States Patent
Calderon et al.

(10) Patent No.: US 10,064,988 B2
(45) Date of Patent: Sep. 4, 2018

(54) BIOLOGICAL FLUID FILTERS WITH PORT FOR OPTIMIZED FLOW DISTRIBUTION

(71) Applicant: Fenwal, Inc., Lake Zurich, IL (US)

(72) Inventors: Carlos Calderon, Waukegan, IL (US); Daniel Lynn, Spring Grove, IL (US); Paolo Verri, Carpi (IT)

(73) Assignee: FENWAL, INC., Lake Zurich, IL (US)

( * ) Notice: Subject to any disclaimer, the term of this patent is extended or adjusted under 35 U.S.C. 154(b) by 88 days.

(21) Appl. No.: 13/923,073

(22) Filed: Jun. 20, 2013

(65) Prior Publication Data

US 2014/0374338 A1 Dec. 25, 2014

(51) Int. Cl.

*A61M 1/36* (2006.01)
*A61M 1/34* (2006.01)
*A61M 1/02* (2006.01)

(52) U.S. Cl.

CPC ............ *A61M 1/34* (2013.01); *A61M 1/0218* (2014.02); *A61M 1/3406* (2014.02); *A61M 1/3633* (2013.01); *A61M 1/3635* (2014.02); *A61M 2206/20* (2013.01)

(58) Field of Classification Search

CPC .... A61M 1/0218; A61M 1/34; A61M 1/3633; A61M 1/3635; A61M 1/3636; A61M 2202/0439; A61M 2005/1657; A61M 2206/12; A61M 2206/20; B01D 63/08
See application file for complete search history.

(56) References Cited

U.S. PATENT DOCUMENTS

| | | | | |
|---|---|---|---|---|
| 4,639,243 | A * | 1/1987 | Schmidt .................. | A61M 1/30 604/6.04 |
| 6,601,710 | B2 * | 8/2003 | Calhoun et al. .............. | 210/435 |
| 7,854,845 | B2 * | 12/2010 | Zuk, Jr. .......................... | 210/645 |
| 2001/0009756 | A1 * | 7/2001 | Hei ..................... | A61M 1/0218 435/2 |
| 2002/0113003 | A1 * | 8/2002 | Lynn et al. ................ | 210/257.1 |
| 2005/0056580 | A1 * | 3/2005 | Reitz et al. ................... | 210/232 |
| 2014/0291227 | A1 | 10/2014 | Ducoroy et al. | |

FOREIGN PATENT DOCUMENTS

| | | | | |
|---|---|---|---|---|
| EP | 0 516 846 A1 | 12/1992 | | |
| EP | 2 042 221 A1 | 4/2009 | | |
| EP | 2783717 A1 | 10/2014 | | |
| EP | 2878316 A1 | 6/2015 | | |
| WO | WO 95/017236 | 6/1995 | | |
| WO | WO 00/062891 | 10/2000 | | |
| WO | WO 2008/103142 | 8/2008 | | |
| WO | WO 2008103142 A1 * | 8/2008 | ............. | A61M 1/36 |

OTHER PUBLICATIONS

European Search Report dated Nov. 9, 2014, for EP Application No. 13193605.6-1651.

* cited by examiner

*Primary Examiner* — Patrick J Orme
(74) *Attorney, Agent, or Firm* — Cook Alez Ltd.

(57) ABSTRACT

Devices for the removal of cells or other particles from a biological fluid are disclosed. The devices include a removal medium housed within a chamber of a housing. The devices include inlet and outlet ports carried by the walls. One or both of the ports includes a flow path portion having a chamber-communicating portion that has a cross-section that is larger than the cross-section of an adjacent flow path portion.

16 Claims, 2 Drawing Sheets

BIOLOGICAL FLUID FILTERS WITH PORT FOR OPTIMIZED FLOW DISTRIBUTION

FIELD OF THE DISCLOSURE

The present disclosure is directed to removal devices for processing biological fluids and removing unwanted components or agents therefrom. More particularly, the present disclosure is directed to removal devices such as filters for processing biological fluids having ports that optimize flow distribution in the removal medium.

BACKGROUND

Removal devices are commonly used in the medical field to remove unwanted components from a biological fluid. For example, in the field of blood processing and collection, it is common to remove leukocytes (white blood cells) from the biological fluid (e.g., blood) prior to transfusion of the collected blood or fluid to a patient, as leukocytes present in transfused blood can often cause adverse reactions in the patient receiving the collected blood or fluid. Typically, the removal device includes a filter medium that has pores sized and distributed to prevent the passage of leukocytes, thus providing a biological fluid that is substantially free of leukocytes.

The biological fluid enters the filter through an inlet port and flows through a filter medium. Typically, the filter medium (for leukoreduction) includes a plurality of sheets made of melt-blown, non-woven fibers which provide a network of pores and torturous path through which the biological fluid must pass. The filter (or other removal device) includes an outlet port on the opposite side of the medium through which the biological fluid exits the device. For effective and time-efficient filtration of the biological fluid, it is desirable that the fluid is well distributed across the membrane. Thus, efforts to provide filters that remove as many leukocytes as possible in a time-efficient manner and optimize the flow of the biological fluid in the removal medium are ongoing.

SUMMARY

In one aspect, the present disclosure is directed to a device for removing unwanted cells from a biological fluid. The device includes a housing including a pair of walls defining a chamber between the walls and a removal medium within the chamber. The device further includes an inlet port carried by one of the pair of walls and an outlet port carried by the other of the pair of walls. At least one of the ports defines a flow path that includes a chamber-communicating portion that has a cross-section larger than the cross-section of an adjacent portion of the flow path within the port.

DETAILED DESCRIPTION OF THE EMBODIMENTS

Figure 1:
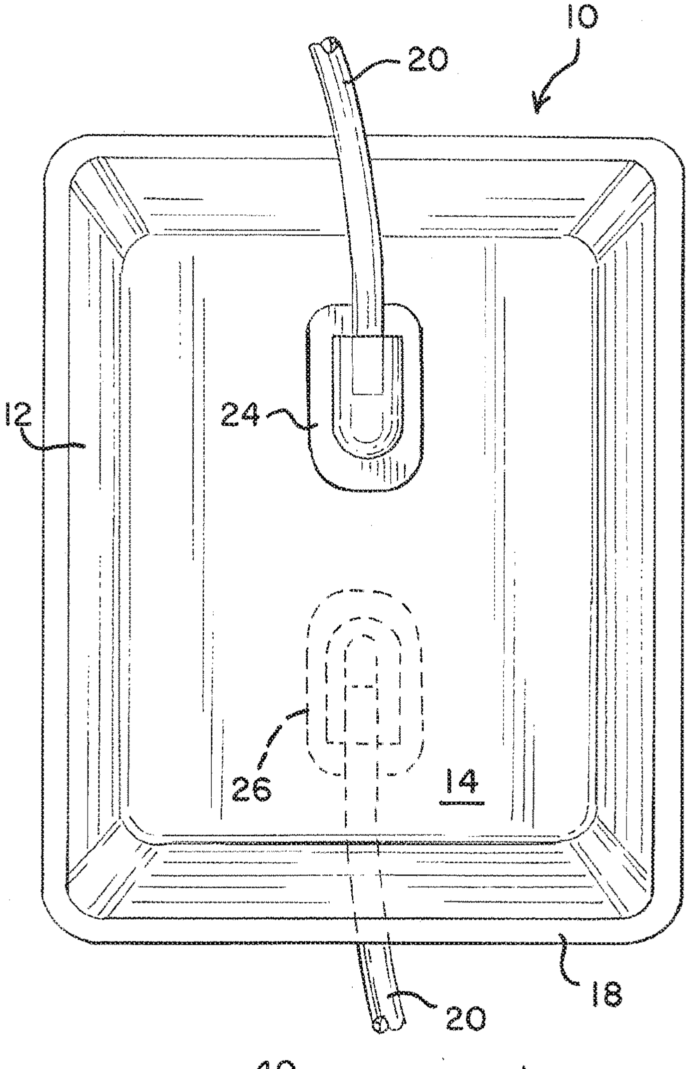
FIG. 1 is a plan view of a representative filter in accordance with the present disclosure.

FIG. 1 shows a representative removal device in accordance with the present disclosure. While the devices described herein are particularly well-suited for leukoreduction, it will be understood that the present disclosure is not limited to the removal of any one component from any one biological fluid. The removal devices described herein may be used wherever it is desired to remove a component or an agent from a biological fluid.

Device 10 is suited for removal of selected components from a biological fluid such as blood. Device 10 includes housing 12, which includes outer walls 14 and 16. Housing 12 is preferably made of a biocompatible material that is also sterilizable using conventional sterilization techniques commonly used in the assembly of disposable blood processing sets, such as steam sterilization or radiation sterilization. In one embodiment, housing walls 14, 16 may be made of a rigid, polymeric material sealed together at or near the periphery thereof. The sealing of walls 14, 16 may be achieved by adhesive, welding or other forms of attachment.

In a preferred embodiment, as shown in FIG. 1, housing walls 14 and 16 may be made of a soft, flexible polymeric material. Examples of suitable polymeric materials include any flexible material such as, but not limited to polyvinyl chloride. As shown in FIG. 1, housing walls may be sealed along their peripheral edges to form a seal 18. In the embodiment of FIG. 1, an additional inner peripheral seal may also be provided, as described in Patent Application Publication US 2002/0113003, the contents of which is incorporated herein by reference. Seal 18 and inner peripheral seal define a cushioned peripheral portion (not shown).

Figure 2:
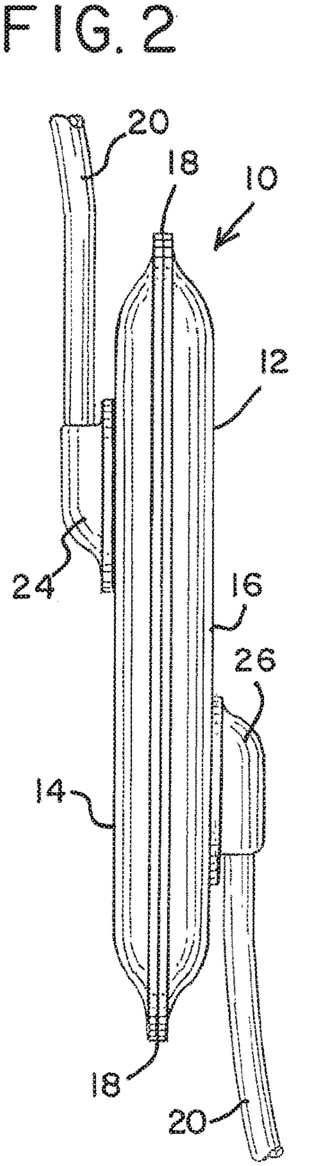
FIG. 2 is a side view of the filter of FIG. 1.

Regardless of the housing material used, walls 14 and 16 may include inlet and outlet ports 24 and 26, respectively. Ports 24 and 26 communicate with an interior chamber 28, defined by walls 14 and 16. Ports 24 and 26 may be carried by walls 14 and 16, as shown in FIGS. 1 and 2. Ports 24 and 26 may be separately attached to housing walls 14, 16 or integrally molded with housing walls 14 and 16. Ports 24, 26 may be made of any suitable material such as, but not limited to, polyvinyl chloride (PVC). A material having a 77 shore A durometer (+/−10) may be preferred. As shown in FIGS. 1 and 2, the inlet and outlet ports may be located in diametrically opposed locations on walls 14 and 16. Thus, inlet port 24 may be positioned closer to the “top” peripheral edge of device 10 on wall 14, whereas outlet port 26 may be positioned closer to the “bottom” peripheral edge of device 10 and wall 16. Of course, it will be appreciated that the location of ports 24 and 26 may be modified or otherwise provided. Ports 24 and 26 define internal flow paths which establish fluid communication between interior chamber 28 (FIG. 5) and joined tubing 20 that leads to other containers or parts of a disposable fluid processing set in which device 10 is included.

Figure 5:
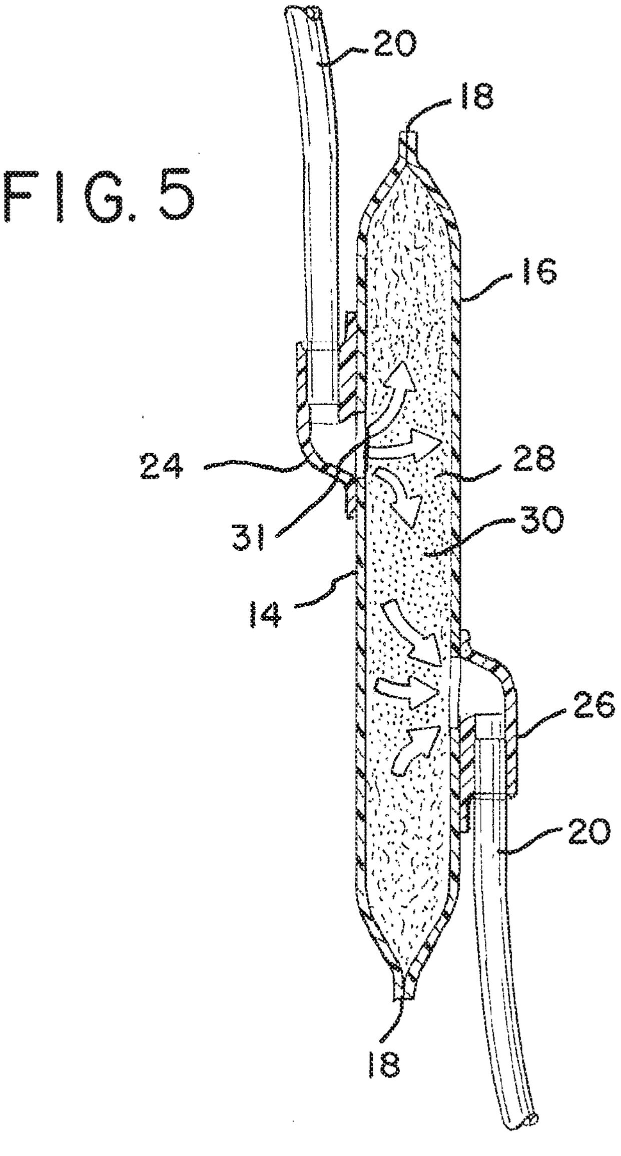
FIG. 5 is a cross-sectional side view of a filter device of the present disclosure showing the distribution of flow across the filter medium.

As shown in FIG. 5, interior chamber 28 accommodates a filter medium 30. In one embodiment, filter medium 30 may be provided as a pad that includes a plurality of pores sized to prevent passage of leukocytes and/or other unwanted components while allowing other blood components to pass. In one embodiment, filter medium 30 may include a plurality of sheets wherein each sheet includes pores of a desired diameter and/or size and distribution. In one embodiment, sheets may be made of melt blown, non-woven fibers. Fibers may be made of a suitable polymeric material, such as polyester, or a polyolefin, such as polyethylene or polypropylene. Depending, in part, on the application, removal medium 30 may also be made of woven fabric or a composite polymeric material.

As noted above, removal medium 30 may be made of a plurality of melt blown, non-woven fiber sheets. In addition, groups of sheets may provide filter medium with filter portions selected to perform particular functions. For example, filter medium 30 may include a filter portion closest to housing wall 14 (carrying inlet port 24) made up of a plurality of sheets to provide a "pre-filter." Downstream of the pre-filter, device 10 may include the "main" filter portion which may include a plurality of sheets of selected porosity. A filter portion downstream of the main filter may provide for filtration of additional components and/or provide a spacer element for the filter medium 30.

Figure 3:
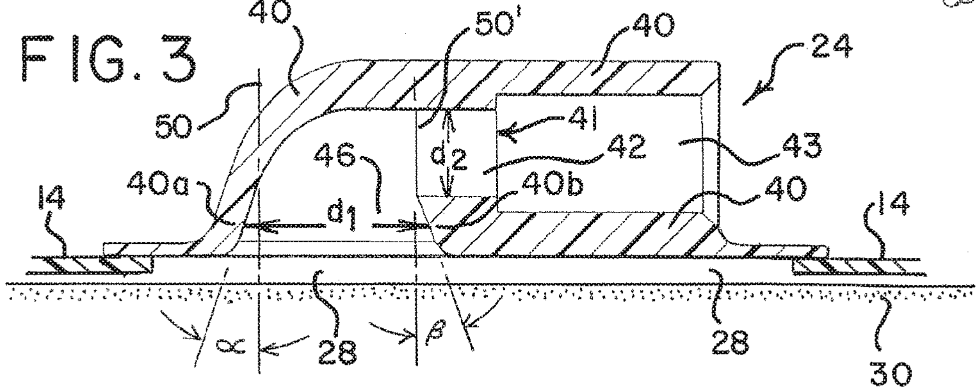
FIG. 3 is an enlarged cross-sectional view of one embodiment of a filter port in accordance with the present disclosure.

As shown in FIG. 3, port 24 includes a flow path 41 defined by port wall 40. Flow path 41 may include a chamber-communicating portion 46 that is adjacent to interior or chamber 28 and directs flow into interior chamber 28 and removal medium 30 contained therein. Flow path 41 may have a variable diameter or cross-section between tube receiving portion 43 (i.e., the portion that receives tubing 20) and interior chamber 28, as defined by the thickness of port wall 40. For example, portion 46 of flow path 41 may have a greater cross-section or diameter $d_1$ than the cross-section or diameter $d_2$ at a portion of the flow path adjacent to portion 42 and (in the case of inlet port 24) upstream of portion 46. Conversely, in the case of outlet port 26, chamber-communicating portion 46 may have a larger cross-section than adjacent flow path portion 42 downstream of portion 46.

A greater cross-section or diameter and, therefore, a wider opening to removal medium 30, allows for better distribution of the biological fluid across removal medium 30, as shown by the arrows in FIG. 5, and more particularly, better flow distribution from the inlet port across the filter media and between the filter media and the outlet port. In one embodiment, port walls 40*a* and 40*b* flare outwardly relative to axes 50 and 50', which axes are generally perpendicular to housing wall 14 and the outer surface 31 of filter medium 30. In one embodiment, walls 40*a* and 40*b* flare outwardly relative to axes 50 and 50' by angles α and β, respectively. The angles formed between flared walls 40*a* and 40*b* and axes 50 and 50' may be anywhere between 10-89° and, more preferably, may be between about 20-60°. The degree of outward flare (i.e., angles α and β) may be identical to provide for a generally symmetrical port opening at portion 46. By way of example, the diameter of the port opening at the chamber-communicating portion as defined by the flared walls 40*a* and 40*b* may be between about 0.25 to 2.0 cm.

Figure 4:
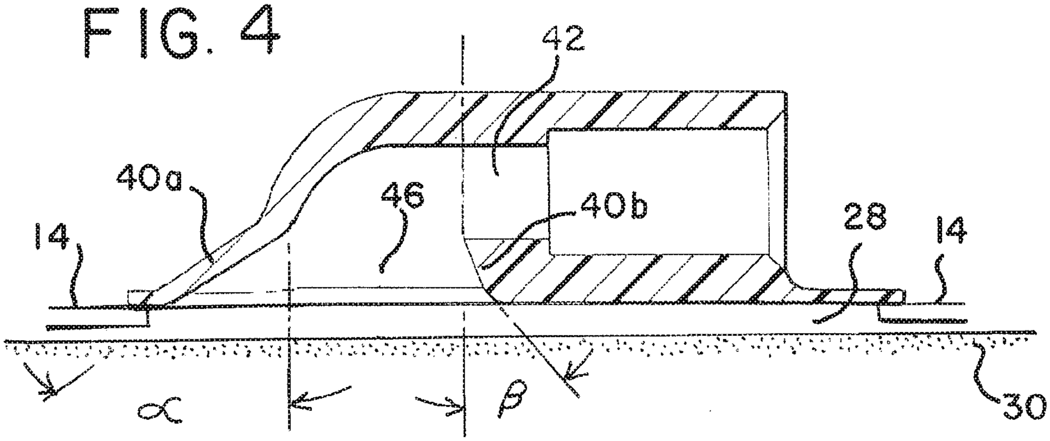
FIG. 4 is an enlarged cross-sectional side view of another embodiment of a filter port in accordance with the present disclosure.

Alternatively, one of walls 40*a* and 40*b* may flare outwardly more than the other to provide an asymmetrical or non-symmetrical opening at portion 46, as shown, for example, in FIG. 4. An asymmetrical or non-symmetrical opening may be desirable where port 24 is not centrally located on filter housing wall 14 (or 16) but is, instead, nearer the "top" (or "bottom") edge of device 10. An asymmetrical opening where port wall 40*a* flares outwardly to a greater degree toward the "bottom" edge than the top edge of filter 10 may allow for greater distribution of fluid within filter medium 30.

It will be appreciated that both ports 24 and 26 may include a structure as described above and that the discussion above, while in the context of port 24, may apply equally to port 26. Alternatively, only one of the ports may be so structured. Thus, in one embodiment, one of ports 24 or 26 may include symmetrically flared port walls 40*a* and 40*b* resulting in a wider flow path while the other port may be non-flared with walls that are generally perpendicular relative to the outer housing wall 14.

Alternatively, one of ports 24 or 26 may have an asymmetrical or non-symmetrical flared wall as described above and shown in FIG. 4, while the other of the ports has no flare whatsoever.

In still a further embodiment, one of ports 24 or 26 may have an asymmetrical opening in communication with interior chamber 28 defined by asymmetrically flared walls 40*a* and 40*b*, while the other of the ports has symmetrical flared walls 40*a* and 40*b*, as shown in FIG. 3.

Finally, in still another embodiment, both of the port openings may be either symmetrically or asymmetrically flared, as described above.

EXAMPLES

Without limiting any of the foregoing, the subject matter described herein may be found in one or more apparatus. For example, in a first aspect of the present subject matter, a device for removing unwanted cells from a biological fluid is set forth. The device includes a housing that includes a pair of walls defining a chamber between the walls. A removal medium is located within the chamber and an inlet port is carried by one of the walls and an outlet port is carried by the other of the walls. At least one of the ports defines a flow path that has a chamber-communicating portion. The chamber-communicating portion has a cross-section that is larger than the cross-section of an adjacent portion of the flow path.

A second aspect of the present subject matter includes the above-described device wherein at least one port includes a wall defining the flow path portions.

A third aspect of the present subject matter includes a device in accordance with any one of the first or second aspects described above wherein the port wall defining the chamber-communicating portion flares outwardly relative to an axis that is substantially perpendicular to the housing wall.

A fourth aspect of the subject matter described herein includes a device in accordance with any one of the first through third aspects described above, wherein the port wall defining the chamber-communicating portion flares outwardly substantially symmetrically.

A fifth aspect of the present subject matter includes the device in accordance with any one of the first through fourth aspects described above wherein the housing has a top end and a bottom end and wherein one of the ports is closer to the top end and the other of the ports is closer to the bottom end.

A sixth aspect of the present subject matter includes a device in accordance with any one of the first through fifth aspects described above wherein each of the ports includes a wall defining the flow path portions.

A seventh aspect of the present subject matter includes a device in accordance with any one of the first through sixth aspects described above wherein the port walls of at least one of the ports defining the chamber-communicating portions flares outwardly relative to an axis that is substantially perpendicular to the housing wall.

An eighth aspect of the present subject matter includes a device in accordance with any one of the second through seventh aspects described above wherein the port wall defines a chamber-communicating portion that flares outwardly substantially symmetrically.

A ninth aspect of the present subject matter includes a device in accordance with any one of the above-described second through seventh aspects wherein the port walls defining the chamber-communicating portion flare outwardly non-symmetrically.

A tenth aspect of the present subject matter includes a device in accordance with any one of the fifth through sixth aspects described above wherein the port nearer the top portion of the housing includes a port wall defining a chamber-communicating portion and wherein the port wall flares outwardly to a greater degree toward the bottom end than toward the top end of the housing.

An eleventh aspect of the present subject matter includes a device in accordance with any one of the first through tenth aspects described above wherein the port nearer the bottom end of the housing includes a port wall defining a chamber-communicating portion wherein the port flares outwardly to a greater degree toward the top end of the housing than toward the bottom end of the housing.

A twelfth aspect of the present subject matter includes a device in accordance with any one of the first through eleventh aspects described above wherein the housing walls are made of a flexible material.

A thirteenth aspect of the present subject matter includes a device in accordance with any one of the first through twelfth aspects described above wherein the ports are integrally molded with the housing walls.

A fourteenth aspect of the present subject matter includes a device in accordance with any one of the first through thirteenth aspects described above wherein the ports are separately molded and separately attached to the housing walls.

A fifthteenth aspect of the present subject matter includes a device in accordance with any one of the first through fourteenth aspects described above wherein the removal medium comprises a filter of non-woven fibers.

A sixteenth aspect of the present subject matter includes a device in accordance with any one of the first through fifteenth aspects described above wherein the removal medium includes a plurality of layers of non-woven fibers.

A seventeenth aspect of the present subject matter includes a device in accordance with any one of the first through sixteenth aspects described above wherein the removal media includes a porous filter for removing leukocytes from blood.

An eighteenth aspect of the present subject matter includes a device in accordance with any one of the first through seventeenth aspects described above wherein the walls are sealed together along the peripheries to provide an outer peripheral seal.

A nineteenth aspect of the present subject matter includes a device in accordance with the eighteenth aspect described above wherein an inner seal is spaced inwardly from the peripheral seal.

A twentieth aspect of the present subject matter includes a device in accordance with any one of the first through nineteenth aspects described above wherein the adjacent portion of the flow path is substantially parallel to the housing.

It should be understood that various changes and modifications to the presently preferred embodiments described herein will be apparent to those skilled in the art. Such changes and modification can be made without departing from the spirit and scope of the invention disclosed herein.

The invention claimed is:

1. A device for removing unwanted cells from a biological fluid comprising:

a) a housing comprising a pair of flexible walls defining an interior chamber between said walls, said housing having a top peripheral edge and a bottom peripheral edge;

b) a removal medium filter of non-woven fibers within said interior chamber;

c) an inlet port carried by one of said pair of housing walls and an outlet port carried by the other of said pair of housing walls, wherein said inlet port is closer to said top peripheral edge and said outlet port is closer to said bottom peripheral edge, said inlet port and said outlet port being located on said housing walls in diametrically opposed positions;

d) each of said ports defining a flow path, said flow path comprising a chamber-communicating portion at said housing wall and an adjacent portion wherein said chamber-communicating portion has a cross-section larger than the cross-section of said adjacent portion, wherein each of said inlet port and said outlet port comprises a flexible flared wall defining said chamber-communicating portion, wherein said flexible flared wall defining said chamber-communicating portion of said inlet port flares non-symmetrically outwardly relative to an axis that is generally perpendicular to said housing wall and wherein said flexible flared wall of said inlet port that is nearer said bottom peripheral edge flares outwardly from said adjacent portion at a greater angle relative to said axis than said flexible flared wall nearer said top peripheral edge, and wherein said chamber-communicating portion of said inlet port does not overlap with said chamber-communicating portion of said outlet port.

2. The device of claim 1 wherein said flexible flared wall of said outlet port defining said chamber-communicating portion flares outwardly relative to an axis that is generally perpendicular to said housing wall.

3. The device of claim 2 wherein said outlet port flexible flared wall defining said chamber-communicating portion of said outlet port flares outwardly symmetrically.

4. The device of claim 2 wherein said one of said outlet port flexible flared walls flares outwardly to a greater degree toward said top peripheral edge than toward said bottom peripheral edge.

5. The device of claim 1 wherein said ports are integrally molded with said housing walls.

6. The device of claim 1 wherein said ports are separately molded and separately attached to said housing walls.

7. The device of claim 1 wherein said removal medium filter comprises a plurality of layers of non-woven fibers.

8. The device of claim 1 wherein said removal medium filter comprises a porous filter for removing leukocytes from blood.

9. The device of claim 1 wherein said flexible walls are sealed together along their peripheries to provide an outer peripheral seal.

10. The device of claim 9 further comprising an inner seal spaced inwardly from said peripheral seal.

11. The device of claim 1 wherein said adjacent portion of said flow path is parallel to said housing.

12. The device of claim 1 wherein said flexible flared wall defining said chamber-communicating portion of said inlet port that is nearer said bottom peripheral edge flares outwardly between said adjacent portion and said housing wall at an angle of no greater than 89° relative to said axis.

13. The device of claim 12 wherein said flexible flared wall defining said chamber communicating portion of said inlet port that is nearer said bottom peripheral edge flares outwardly up to 60° relative to said axis.

14. The device of claim 1 wherein said chamber-communicating flow path portion has a diameter of about 0.25 to 2.0 cm.

15. The device of claim 1 wherein said inlet port flexible flared wall that is nearer said bottom peripheral edge includes only one flared wall portion between said adjacent portion and said housing wall.

16. The device of claim 15 wherein no part of said flared wall portion forms an angle greater than 89° relative to said axis.

* * * * *